United States Patent [19]

Hochgraeber et al.

[11] Patent Number: 5,502,389
[45] Date of Patent: Mar. 26, 1996

[54] APPARATUS FOR POLYELECTROLYTE MEASUREMENT WITH AN ULTRASONICALLY DRIVEN LINER

[75] Inventors: Hermann Hochgraeber, Seefeld; Lutz Pickelmann, Munich, both of Germany

[73] Assignee: Mutek Analytic GmbH, Herrsching, Germany

[21] Appl. No.: 251,916

[22] Filed: Jun. 1, 1994

[30] Foreign Application Priority Data

May 3, 1994 [EP] European Pat. Off. .............. 94106918

[51] Int. Cl.⁶ .................................................. G01N 27/60
[52] U.S. Cl. .......................... 324/453; 324/71.1; 324/450; 73/864.91
[58] Field of Search ..................... 324/71.1, 425, 324/439, 450, 453; 73/863, 864.91; 204/193, 194

[56] References Cited

U.S. PATENT DOCUMENTS

| | | | |
|---|---|---|---|
| 3,368,145 | 2/1968 | Gerdes | 324/453 |
| 3,614,602 | 10/1971 | Ciotti | 324/453 |
| 3,781,675 | 12/1973 | Angel | 324/450 X |
| 4,297,640 | 10/1981 | Moore | 324/458 |
| 4,446,435 | 5/1984 | Canzoneri | 324/453 |
| 4,449,101 | 5/1984 | Canzoneri et al. | 324/453 |
| 4,769,608 | 9/1988 | Bryant | 324/453 |
| 4,961,147 | 10/1990 | Moore | 324/71.1 |
| 5,119,029 | 6/1992 | Bryant et al. | 324/453 |
| 5,202,016 | 4/1993 | Church et al. | 324/453 X |
| 5,408,185 | 4/1995 | Krah | 324/453 |

FOREIGN PATENT DOCUMENTS

| | | | |
|---|---|---|---|
| 4008916 | 5/1991 | Germany . | |
| 5269449 | 10/1993 | Japan . | |
| 1089833 | 11/1967 | United Kingdom | 324/450 |
| WO9114940 | 10/1991 | WIPO . | |

OTHER PUBLICATIONS

"Analysis Instrumentation, vol. 4", Proceedings of the Twelfth Annual Analysis Instrumentation Symposium, May 11–13, 1966, Houston, Texas, pp. 181–198.

*Primary Examiner*—Kenneth A. Wieder
*Assistant Examiner*—Diep Do
*Attorney, Agent, or Firm*—Knobbe Martens Olson & Bear

[57] ABSTRACT

An apparatus for automated polyelectrolyte measurement in process materials comprises a sample vessel with an outer wall defining a cylindrical cavity and with a reservoir of larger diameter above and in communication with the cavity. A liner for the cavity and the reservoir are made of an electrically insulating material such as polytetrafluoroethylene. To clean the apparatus there is also provided an ultrasonic oscillator which is mechanically coupled to the sample vessel. In order to improve the cleaning process, the liner and preferably also the reservoir are attached to the outer wall in such a way as to resist tensile and shear forces and the ultrasonic oscillator is attached to the outer wall. Preferably, the liner is attached to the outer wall by an adhesive.

12 Claims, 4 Drawing Sheets

5,502,389

APPARATUS FOR POLYELECTROLYTE MEASUREMENT WITH AN ULTRASONICALLY DRIVEN LINER

FIELD OF THE INVENTION

The present invention relates to an apparatus for polyelectrolyte measurement.

DESCRIPTION OF THE PRIOR ART

In the U.S. publication "12th Material ISA Analysis Instr. Symposium, Houston, Tex., 1966: Vol. 4, pages 181–198" apparatus for polyelectrolyte measurement is described, by means of which samples for the measurement of polyelectrolyte consumption in a process are introduced by hand into a sample vessel and a piston disposed within the sample vessel is moved. This movement generates a streaming potential which is recorded and measured by way of electrodes. At the same time, titration is carried out. After each measurement procedure the sample vessel and the piston must be taken apart and cleaned.

In German Patent Specification DE 40 08 916 C1 an apparatus of the kind just cited is described, in which polyelectrolyte measurement can be performed automatically. This known apparatus will now be described in detail with reference to the attached FIG. 7.

FIG. 7 is a partial longitudinal section of the known apparatus, in which a sample vessel 30 is provided which comprises an inner insulating block 37 and an outer metal part consisting of an outer wall 38 and a floor 39. A bore formed substantially in the middle of the insulating block 37 defines a cylindrical cavity 31, the upper end of which is continuous with a larger-diameter, also cylindrical reservoir 32. At the upper end of the cylindrical cavity 31 there is an annular indentation 36, within which is fixed an annular first electrode 34 made of a non-corroding metal. The floor 39 closes off the cylindrical cavity 31 at its lower end and forms a second electrode 35 at this site.

The electrodes 34 and 35 are connected to the inputs of an amplifier 56, the output of which is connected to an input of a control mechanism 22.

The floor 39 is integral with a flared section 40, onto the end of which two annular piezoelectric oscillators, stacked one above the other, are pressed by means of a screw bolt 48 and an intermediately positioned washer 47. Between the piezo rings 44, 45 is inserted an electrode 46. The arrangement is such that the outer annular surfaces of the two piezo rings 44, 45 are in electrical contact with one another by way of the bolt 48, so that the two piezo rings 44, 45 are electrically in parallel and mechanically in series. They are controlled electrically by way of the electrode 46 and the metal parts 39, 40, 47 and 48, by an ultrasound generator 54 the output of which is passed through a driver amplifier 55. The arrangement includes electrical feedback so that the oscillation frequency can be automatically adjusted to an optimal value.

In the bottom end surface of the insulating block 37 is cut a radial channel 41 to provide an outwardly directed duct with a part-circular cross section, formed by the walls of the channel and by the floor 39. Where the channel 41 meets the outer wall 38 there is a hole in the latter adjoining a connection piece 42. To the connection piece 42 is attached a conduit leading to an outlet valve 28, by way of which the connection piece 42 is connected to an outlet pipe 29. The outlet valve 28 is connected to the controller 22 by way of a control line.

Inserted into the cylindrical cavity 31 is a piston 33, which is made of electrically insulating material and is dimensioned so that there is a very narrow gap of the order of a few tenths of a millimeter between the outer surface of the piston and the surface of the insulating block 37 defining the cylindrical cavity 31. The piston 33 has a planar end surface and at its opposite end is joined by a shaft 49 to a crank 51 that can be rotated by an electrical motor 52. An angle indicator 53 is attached to the crank 51 to monitor the angle of rotation of the crank 51, which is a measure of the vertical position of the piston 33, and to signal it to the controller 22. The motor 52 can be adjusted by the controller 22 by way of a driver amplifier 57, so that the actuation 50 of the piston 33 can be precisely regulated.

Opening into the reservoir section 32 is a rinsing duct 26, which can be connected to a container filled with distilled water by way of a solenoid valve 27 controlled by the controller 22. A titration duct 24 also opens into the reservoir section 32 and can be connected to a container in which the titration fluid is stored by way of a solenoid valve 25 controlled by the controller 22. Finally, a sample of the liquid to be tested can be introduced to the sample vessel by way of a duct 19 that opens into the reservoir section 32. This introduction of a sample is also carried out under the control of the controller 22.

The operation of the apparatus shown in FIG. 7 will now be described.

A predetermined amount of a sample is introduced into the reservoir section 32 by way of the duct 19. The piston 33 is reciprocated by the actuating means 50. The streaming potential so produced is conducted to the controller 22 by way of the electrodes 34, 35 and the amplifier 56. The controller 22 processes the signal and indicates or records the measured value by way of a measuring device 58. At the same time, titration is performed by way of the duct 24.

After the measurement has been completed, the valve 28 is opened during each downstroke of the piston 33 and closed during each upstroke. As a result, all the liquid contained in the apparatus is pumped into the outlet pipe 29 and can be discarded. After the pumping has proceeded for a time sufficient to ensure that no appreciable quantity of sample remains in the vessel, the rinsing valve 27 is opened so that rinsing fluid can enter the reservoir section 32 by way of the duct 26. As it does so, the piston 33 continues to reciprocate, the valve 28 opening and closing in synchrony with this motion as described above. At the same time the ultrasound generator 54 is turned on by the controller 22, so that ultrasonic oscillation is induced in the rinsing fluid. The cavitation action of the ultrasonic oscillation of the fluid, in combination with the flow of the rinsing fluid through the chamber while the piston 33 is moving, is intended to ensure thorough cleaning of the parts that are in contact with the sample.

It has now been found that the results obtained with this known arrangement have a relatively broad scatter, and in particular depend both on the duration of use of the apparatus and on the nature of the substances being investigated.

SUMMARY OF THE INVENTION

The object of the present invention is to provide an apparatus of the kind described above in which precision of the measurements taken is improved.

According to the present invention there is provided an apparatus for automated polyelectrolyte measurement of a substance comprising a sample vessel with an outer wall defining a cylindrical cavity, a liner disposed within the cylindrical cavity and made of an electrically insulating material, a reservoir of larger diameter than said cylindrical cavity and located above and in communication with said cavity, electrodes substantially located one at each end of said cylindrical cavity respectively, an electrically insulating piston reciprocable within said cylindrical cavity, a means for measuring a charge displacement between said electrodes, an outlet duct located at the bottom of said cylindrical cavity, an ultrasound generator, and an ultrasonic oscillator which is coupled mechanically to the sample vessel and which, during a rinsing procedure, is actuated by the ultrasound generator in such a way as to induce ultrasonic oscillations in the rinsing liquid, and wherein the improvement comprises the liner being attached to the outer wall in such a way as to resist tensile and shear forces and the ultrasonic oscillator being connected to the outer wall.

In the present invention the ultrasonic oscillations are induced in the rinsing fluid to a greater degree than in a conventional arrangement. Furthermore, in the arrangement in accordance with the invention all parts of the apparatus that come into contact with the sample fluid are made of electrically insulating material. Thus, no metal floor is necessary to transmit the ultrasonic oscillations into the rinsing fluid. This in turn allows the electrodes to be made of noble metals, in particular platinum, without excessive cost. Such electrodes improve the measurement precision, specifically the reproducibility of the measurements. It is also important that both tensile and shear forces are transmitted into the insulating material and hence into the liquid. Owing to the firm connection between the liner and the outer wall, for example by way of adhesive, sputtering, chemical coating etc., this transmission is ensured.

Preferably, the liner and the reservoir are formed integrally together with a connection piece which defines said outlet duct. Such construction avoid or least substantially mitigates problems in making the vessel watertight.

Preferably also, the ultrasonic oscillator is coupled to that portion of the outer wall which defines said cylindrical cavity. This arrangement improves the cleaning action.

Preferably also, the ultrasonic oscillator is coupled to the outer wall in such a way that oscillations are transmitted in a direction substantially radially to a long axis of said cylindrical cavity. This is preferably achieved by constructing the ultrasonic oscillator of two substantially identically formed individual oscillators, which are attached to opposite sides of the outer wall. An effective arrangement is thus obtained in a simple manner.

In this case the individual oscillators can also be held onto the outer wall with a specified pressure by means of a gripping yoke that surrounds the individual oscillators or the outer wall. This arrangement allows highly efficient transmission of oscillations from piezo oscillators to the outer wall and into the liquid.

The outer wall is provided with flattened areas in the region of the ultrasonic oscillator, to enable a firm coupling.

An oscillation sensor is also preferably provided, coupled to the sample vessel. This oscillation sensor generates an output signal corresponding to the mechanical oscillations induced in the sample vessel. The output signal is included in a feedback loop of the oscillation generator in such a way that the output frequency of the oscillation generator is adjusted to a value at which the amplitude measured by the oscillation sensor is maximal. That is, the feedback here is not purely electrical as in the known object; instead, the actual oscillations are measured and the oscillation frequency of the ultrasound generator is adjusted in accordance with their amplitude. Thus all mechanical and electrical components involved in the "oscillation process" are included.

The manufacture of the apparatus so constructed advantageously proceeds in the following steps:

First the outer wall with a predetermined inner cavity is produced, e.g. by being turned from a piece of metal.

In addition, an inner block is produced from an insulating material, in particular polytetrafluoroethylene, with an outer diameter that corresponds substantially to the predetermined inner cavity of the outer wall.

The inner block is now glued into the outer wall. When polytetrafluoroethylene is used as the material of the inner block, the material must be pretreated in a manner known per se.

In a last step, the inner block when glued into the outer wall is machined into its final shape. In particular, in this step the portion within the cylindrical cavity within which the piston moves is machined out to form a very thin lining wall, so that the ultrasonic oscillations induced in this region are very little attenuated by the softer plastic material.

Preferably, the inner block is initially manufactured, prior to its being glued into the outer wall, with substantially the same shape as that which will be its final shape that relatively little final processing is required during the definitive machining procedure. However, the cavities so provided are such that the prepared block retains adequate stability.

It is particularly advantageous during the initial preparation of the cavities (before fixation to the outer wall) to shape the reservoir section and part of the outlet duct, namely a connection piece for a hose, in a substantially finished form.

By giving the sample vessel and/or the piston the shape of a cone, it is possible to adjust the gap that determines the potential or the streaming velocity defined by that gap in combination with the piston velocity.

The present invention will now be described by way of example with reference to the accompanying drawings.

DESCRIPTION OF THE PREFERRED EMBODIMENTS

Figure 7:
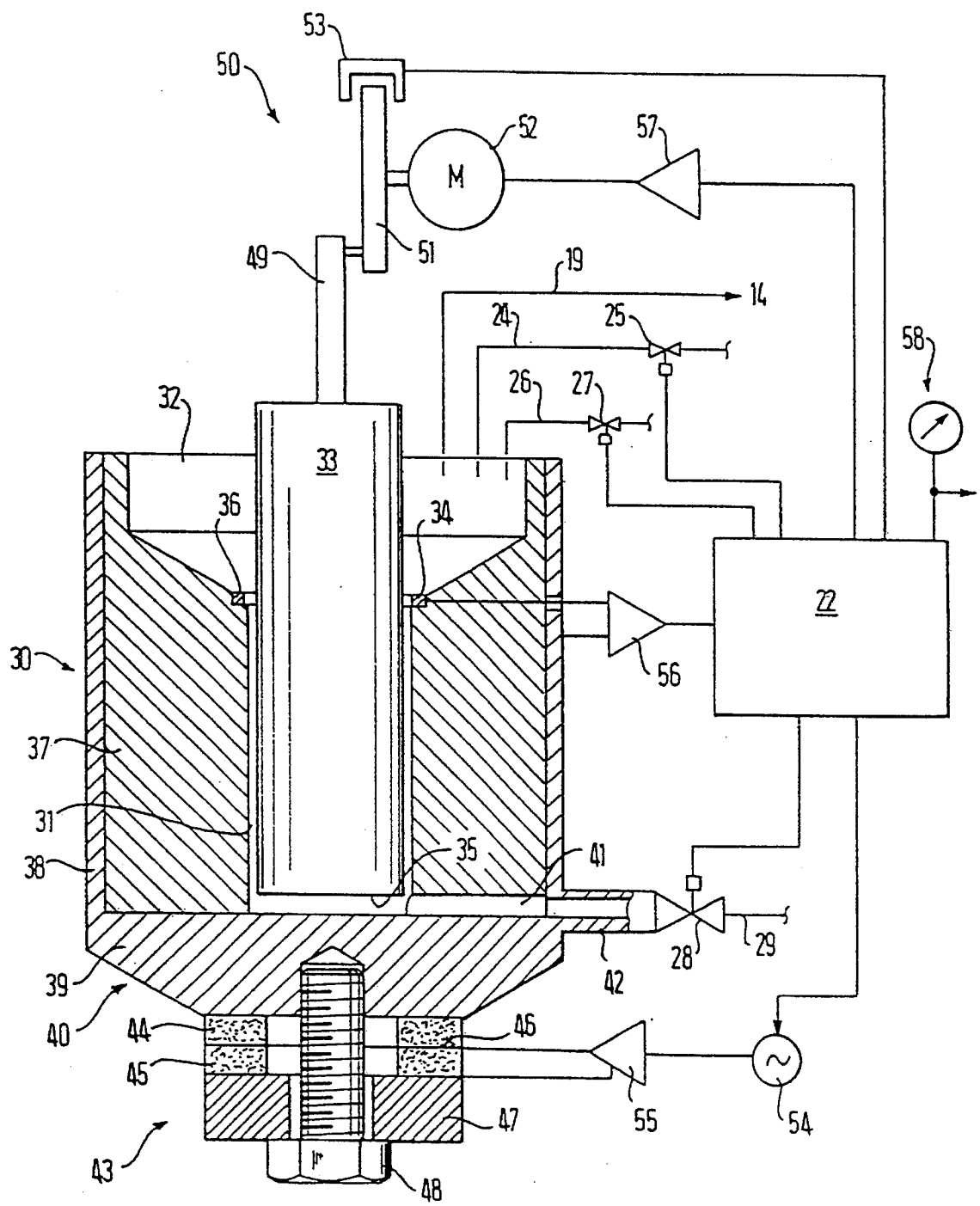
FIG. 7 is a diagram of a conventional apparatus for polyelectrolyte measurement.

In the following description, the components of the apparatus already described previously with reference to FIG. 7 will not be described in detail again insofar as they are conventional.

Figure 1:
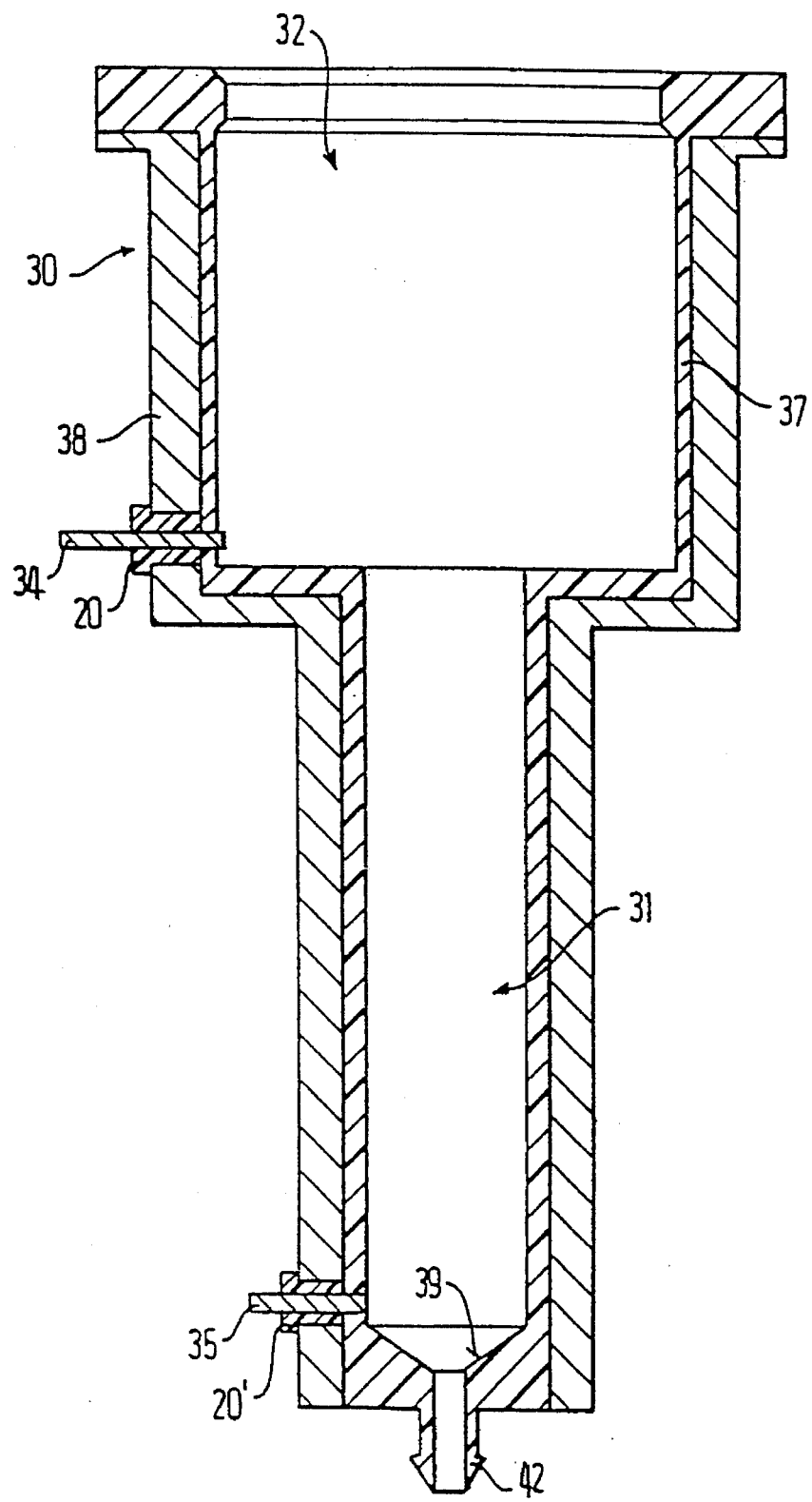
FIG. 1 is a longitudinal section of an apparatus according to the invention.

As shown in FIG. 1, the apparatus in accordance with the invention comprises a sample vessel 30, the outer wall 38 of which is substantially cylindrical in shape with two sections of different diameter.

The upper section forms a reservoir 32 of larger diameter, whereas the lower region forms a cylindrical cavity 31 of smaller diameter.

In the interior of the outer wall 38 an insulating block or liner 37 is provided that not only lines the side walls of the sample vessel 30 but also forms its floor 39. To the floor 39 is appended the connecting piece 42, to which an outlet pipe 29 (not shown here) can be attached.

In the reservoir 32, at about the level of the transition to the smaller-diameter cylindrical section 31, there is provided an upper electrode 34 that extends through a watertight channel in the outer wall 38 and the plastics liner 37, within an insulating sleeve 20. In the lower region of the vessel 30, a lower electrode 35 is provided in the region of the floor 39, which similarly extends through a watertight channel in the outer wall 38 within an insulating sleeve 20'. The two electrodes 34, 35 are made of a noble metal or coated with such a metal.

Figure 2:
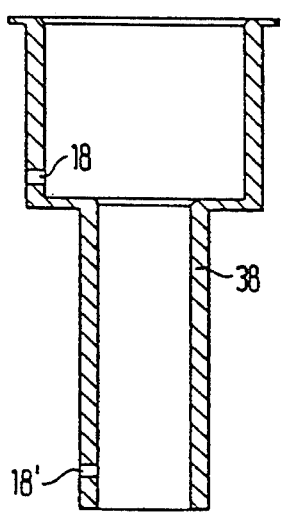
FIG. 2 is a longitudinal section of an outer wall of the apparatus.
Figure 3:
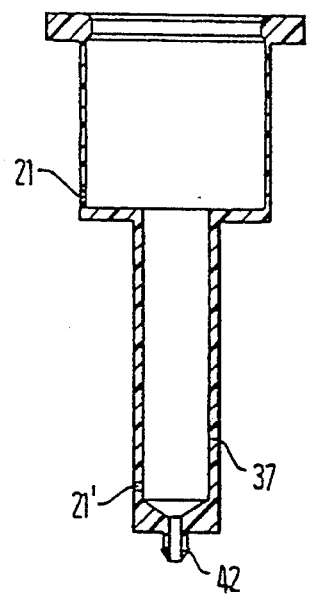
FIG. 3 is a longitudinal section of an inner liner of the apparatus.
Figure 4:
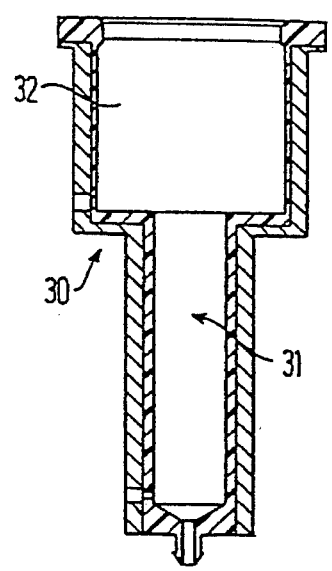
FIG. 4 is a longitudinal section of the outer wall assembled with the liner.
Figure 2A:
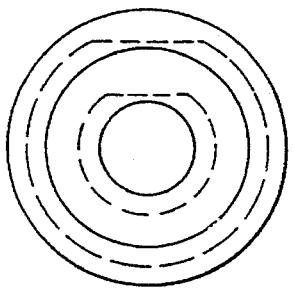
FIG. 2A is a plan view of the outer wall shown in FIG. 2.
Figure 3A:
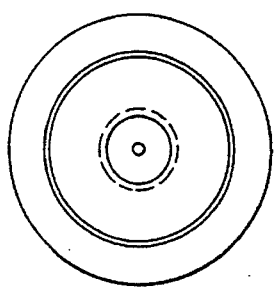
FIG. 3A is a plan view of the liner shown in FIG. 3.
Figure 4A:
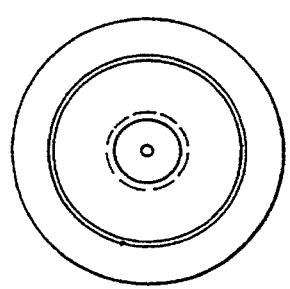
FIG. 4A is a plan view of the assembly shown in FIG. 4.

To manufacture the sample vessel 30, first the outer wall 38 as shown in FIGS. 2,2A is produced and provided with bores 18, 18'. In addition, the insulating liner 37, which is made of polytetrafluoroethylene, is produced with a configuration such that its outer contours correspond to the inner contours of the outer wall 38 as shown in FIGS. 3,3A. Then the insulating liner 37 is pretreated on its outer surface so that it can be coated with an adhesive and fitted closely into the outer wall 38 for permanent fixation. The resulting sample vessel 30 as shown in FIGS. 4,4A is then machined in its interior so that the wall of the insulating liner 37 in the cylindrical cavity 31 is made very thin. Finally, the outer wall 38 is provided in its smaller-diameter region with two flattened surfaces on opposite sides, the first of which can also be provided in the process of manufacturing the outer wall as shown in FIG. 2A.

The construction of an ultrasonic oscillator 43 will now be described with reference to FIGS. 5 and 6.

The ultrasonic oscillator 43 comprises two pairs of piezo rings 44,45 and 44',45', each pair being separated by a contact disk 2,2'. The rings 44,45 and 44',45' are mounted on the outer wall 38 in the region of the said flattened areas. To each of the outer piezo rings 44, 44', on its surface facing away from the outer wall, there is applied a shoe 3, 3' that is seated by a central ball bearing 4, 4' in bearing depressions in an upper and a lower yoke 5, 5'.

The two yokes 5, 5' are held together under tension by screw bolts 6,6' that connect the two yokes 5,5' with one another by way of nuts 8, 8' and underlying spring washers 7,7'. This arrangement ensures that the pressure with which the piezo rings 44,44' and 44',45' are pressed against the outer wall 38 is uniformly distributed over the surface of the piezo rings. The spring washers 7,7' serve to maintain a constant pressure in spite of temperature fluctuations.

The piezo rings 44, 45 and 44', 45' are connected to an amplifier 55, as described above with reference to FIG. 7, in a known manner. The amplifier 55 receives input from an ultrasound generator 54, as also described above with reference to FIG. 7.

Figure 5:
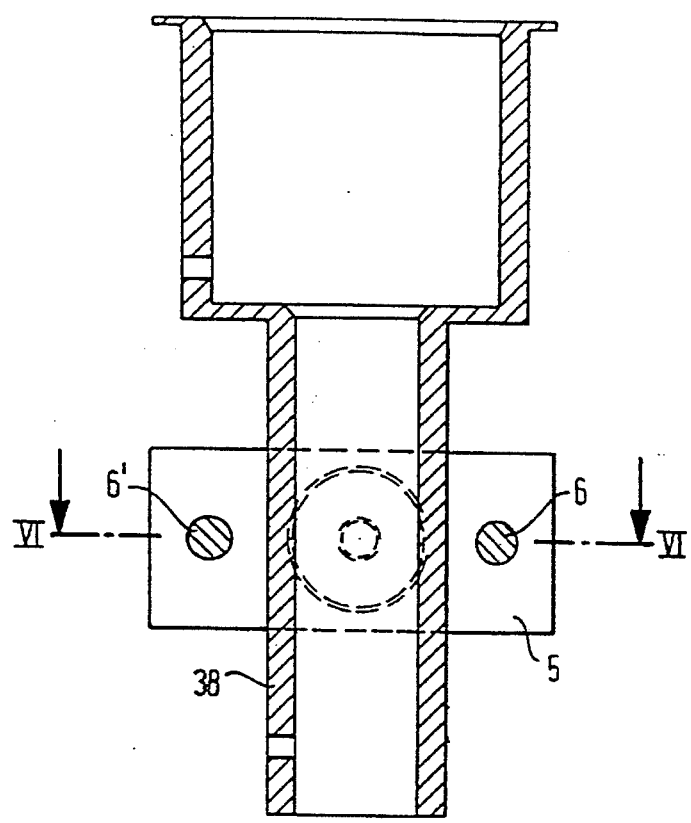
FIG. 5 is a longitudinal section of the outer wall with an ultrasonic oscilator attached thereto.
Figure 6:
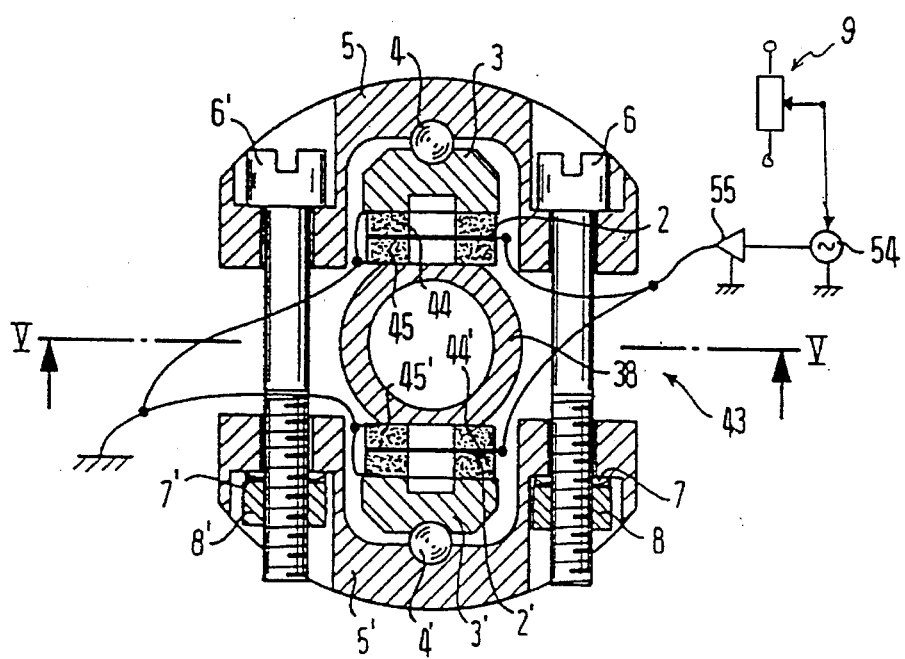
FIG. 6 is a section along the line VI—VI in FIG. 5.

In contrast to the known arrangement, the apparatus of the present invention provides a frequency adjustment element (9) shown in FIG. 5, whose output signal is sent to the ultrasound generator (54). This arrangement allows control adjustment of the ultrasound generator (54) in such a manner that the ultrasonic oscillator (43) receives a frequency at which optimal cleaning of the sample vessel is achieved. In particular, by appropriately adjusting the frequency, certain locations in the sample vessel highly prone to contamination can be intensively cleaned, for example the running area of the piston (33) or in the region of the floor (39). This may be necessary depending on the type of sample investigated.

In another embodiment, the frequency is adjusted to various values in sequence, so that different regions of the vessel are intensively treated sequentially. A frequency combination comprising the mentioned individual frequencies can also be advantageously applied. When the ultrasound generator (54) is provided with a feedback circuit, for example, as an oscillation sensor (not shown) attached to the outer wall (38), the given individual frequencies can be selected by means of electrical filters in the circuit and adapted to the given sample, or sample vessel.

What is claimed is:

1. An apparatus for automated polyelectrolyte measurement of a substance, comprising:

a sample vessel with an outer wall defining within said wall a cylindrical cavity;

a liner disposed within the cylindrical cavity and made of an electrically insulating material, the liner being attached to the outer wall in such a way to resist and transmit tensile and shear forces during ultrasonic oscillations;

a reservoir of larger diameter than said cylindrical cavity and located above and in communication with said cavity;

electrodes extending from outside said outer wall into said cylindrical cavity, said electrodes located one at each end of said cylindrical cavity, respectively;

a means for measuring a charge displacement between said electrodes;

an ultrasound generator; and an ultrasonic oscillator which is coupled mechanically to the outer wall of said sample vessel so as to transmit ultrasonic oscillations to the sample vessel and which, during a rinsing procedure, is actuated by the ultrasound generator in such a way as to induce ultrasonic oscillations in a rinsing liquid within said cylindrical cavity, the output frequency of the ultrasound generator being adjustable depending on a sample to be measured.

2. An apparatus as claimed in claim 1, wherein the liner is further disposed within the reservoir and is also attached to the outer wall and the reservoir in such a way as to resist and transmit tensile and shear forces during ultrasonic oscillation.

3. An apparatus as claimed in claim 1, wherein the liner is formed integrally together with an outlet duct extending through said outer wall at the bottom of said cylindrical cavity.

4. An apparatus as claimed in claim 1, wherein the ultrasonic oscillator is coupled to that portion of the outer wall which defines said cylindrical cavity.

5. An apparatus as claimed in claim 1, wherein the ultrasonic oscillator is coupled to the outer wall in such a way that oscillations are transmitted in a direction substantially radially to a long axis of said cylindrical cavity.

6. An apparatus as claimed in claim 1, wherein liner is attached to the outer wall by an adhesive.

7. An apparatus as claimed in claim 1, wherein the liner is formed onto the outer wall as a coating.

8. A sample vessel for use in an automated polyelectrolyte measurement apparatus, comprising:

a rigid outer wall having an upper cylindrical portion of a first diameter and a lower cylindrical portion of a second diameter, the second diameter being smaller than said first diameter to form a step between the upper portion and the lower portion;

an electrically insulating liner disposed within said outer wall to conform to the inner surfaces of the upper portion and the lower portion, said liner defining a reservoir in said upper portion, and a cylindrical cavity within said lower portion, said liner including a floor defining a bottom of said cylindrical cavity, and being very thin so as not to attenuate ultrasonic oscillations;

a first electrode extending through said outer wall and said liner at a location just above said step;

a second electrode extending through said outer wall and said liner at a location just above said floor; and an ultrasonic oscillator which is coupled mechanically to said outer wall at a location surrounding said lower portion, said ultrasonic oscillator inducing ultrasonic oscillations in a rinsing liquid provided in said cylindrical cavity, said liner being attached to the inner surface of the outer wall in such a way as to resist and transmit tensile and shear forces during ultrasonic oscillation.

9. The sample vessel of claim 8, wherein said liner is attached to the inner surface of the outer wall by an adhesive.

10. The sample vessel of claim 8, wherein the liner is formed on the inner surface of the outer wall as a chemical coating.

11. The sample vessel of claim 8, wherein the liner is sputtered on the inner surface of the outer wall as a coating.

12. The sample vessel of claim 8, wherein said ultrasonic oscillator is coupled to said liner so as to cause ultrasonic oscillations to be transmitted in a direction substantially radially to a long axis of said cylindrical cavity.

* * * * *